(12) United States Patent
Kim et al.

(10) Patent No.: US 8,306,621 B2
(45) Date of Patent: *Nov. 6, 2012

(54) CARDIAC CYCLE SYNCHRONIZED SAMPLING OF IMPEDANCE SIGNAL

(75) Inventors: Jaeho Kim, Redmond, WA (US); Quan Ni, White Bear Lake, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 938 days.

This patent is subject to a terminal disclaimer.

(21) Appl. No.: 11/676,067

(22) Filed: Feb. 16, 2007

(65) Prior Publication Data

US 2007/0142867 A1 Jun. 21, 2007

Related U.S. Application Data

(63) Continuation of application No. 10/612,388, filed on Jul. 2, 2003, now Pat. No. 7,200,440.

(51) Int. Cl.
*A61N 1/365* (2006.01)
(52) U.S. Cl. .............. 607/18; 607/17; 607/20; 600/533; 600/547
(58) Field of Classification Search .............. 607/17, 607/18, 2–9, 42
See application file for complete search history.

(56) References Cited

U.S. PATENT DOCUMENTS

| | | | |
|---|---|---|---|
| 3,593,718 A | 7/1971 | Krasner | |
| 3,896,817 A | 7/1975 | Hursen et al. | |
| 4,009,721 A | 3/1977 | Alcidi | |
| 4,140,132 A | 2/1979 | Dahl | |
| 4,228,803 A | 10/1980 | Rickards | |
| 4,291,699 A | 9/1981 | Geddes et al. | |
| 4,399,820 A | 8/1983 | Wirtzfeld et al. | |
| 4,428,378 A | 1/1984 | Anderson et al. | |
| 4,510,944 A | 4/1985 | Porges | |
| 4,519,395 A | 5/1985 | Hrushesky | |
| 4,543,954 A | 10/1985 | Cook et al. | |
| 4,562,843 A | 1/1986 | Djordjevich et al. | |
| 4,596,251 A | 6/1986 | Plicchi et al. | |
| 4,686,987 A | 8/1987 | Salo et al. | |

(Continued)

FOREIGN PATENT DOCUMENTS

DE 28 05 482 3/1987

(Continued)

OTHER PUBLICATIONS

"BioZ(r) ICG Module", http://web.archive.org/web/20010701105207/http://www.cardiodynamics.com/cdprod50.html (archived on Jul. 1, 2001), 1 page.

(Continued)

*Primary Examiner* — Carl H Layno
*Assistant Examiner* — Allen Potter, Jr.
(74) *Attorney, Agent, or Firm* — Schwegman Lundberg & Woessner, P.A.

(57) ABSTRACT

A cardiac rhythm management device for obtaining transthoracic impedance. The device comprises a sensor for obtaining a signal indicative of an action of a heart, an impedance measurement circuit adapted to measure transthoracic impedance and a processor for utilizing the signal indicative of the action of the heart to sample the transthoracic impedance at sampling intervals commenced by fiducial markers in the signal indicative of the action of the heart, where the sampling of the impedance signal removes the component of a stroke volume of the heart from the signal and thereby provides lung ventilation information.

26 Claims, 9 Drawing Sheets

U.S. PATENT DOCUMENTS

| | | |
|---|---|---|
| 4,702,253 A | 10/1987 | Nappholz et al. |
| 4,722,351 A | 2/1988 | Phillipps et al. |
| 4,773,401 A | 9/1988 | Citak et al. |
| 4,781,201 A | 11/1988 | Wright et al. |
| 4,827,935 A | 5/1989 | Geddes et al. |
| 4,830,008 A | 5/1989 | Meer |
| 4,858,611 A | 8/1989 | Elliott |
| 4,899,752 A | 2/1990 | Cohen |
| 4,901,725 A | 2/1990 | Nappholz et al. |
| 4,930,518 A | 6/1990 | Hrushesky |
| 4,960,129 A | 10/1990 | dePaola et al. |
| 4,966,146 A | 10/1990 | Webb et al. |
| 5,003,976 A | 4/1991 | Alt |
| 5,014,698 A | 5/1991 | Cohen |
| 5,027,813 A | 7/1991 | Pederson et al. |
| 5,063,927 A | 11/1991 | Webb et al. |
| 5,074,303 A | 12/1991 | Hauck |
| 5,085,215 A | 2/1992 | Nappholz et al. |
| 5,085,583 A | 2/1992 | Amos et al. |
| 5,105,819 A | 4/1992 | Wollschlager et al. |
| 5,107,850 A | 4/1992 | Olive |
| 5,127,401 A | 7/1992 | Grevious et al. |
| 5,137,019 A | 8/1992 | Pederson et al. |
| 5,154,171 A * | 10/1992 | Chirife ............................ 607/24 |
| 5,156,147 A | 10/1992 | Warren et al. |
| 5,174,286 A | 12/1992 | Chirife |
| 5,179,946 A | 1/1993 | Weiss |
| 5,190,035 A | 3/1993 | Salo et al. |
| 5,197,467 A | 3/1993 | Steinhaus et al. |
| 5,199,428 A | 4/1993 | Obel et al. |
| 5,201,808 A | 4/1993 | Steinhaus et al. |
| 5,203,326 A | 4/1993 | Collins |
| 5,235,237 A | 8/1993 | Leonhardt |
| 5,235,976 A | 8/1993 | Spinelli |
| 5,249,572 A | 10/1993 | Bonnet |
| 5,269,301 A | 12/1993 | Cohen |
| 5,271,395 A | 12/1993 | Wahlstrand et al. |
| 5,273,034 A | 12/1993 | Nilsson |
| 5,284,136 A | 2/1994 | Hauck et al. |
| 5,300,093 A | 4/1994 | Koestner et al. |
| 5,300,094 A | 4/1994 | Kallok et al. |
| 5,303,702 A | 4/1994 | Bonnet et al. |
| 5,309,917 A | 5/1994 | Wang et al. |
| 5,314,449 A | 5/1994 | Lindgren |
| 5,318,597 A | 6/1994 | Hauck et al. |
| 5,341,811 A | 8/1994 | Cano |
| 5,354,317 A | 10/1994 | Alt |
| 5,379,776 A | 1/1995 | Murphy et al. |
| 5,383,473 A | 1/1995 | Moberg |
| 5,391,190 A | 2/1995 | Pederson et al. |
| 5,423,870 A | 6/1995 | Olive et al. |
| 5,423,883 A | 6/1995 | Helland |
| 5,431,687 A | 7/1995 | Kroll |
| 5,431,693 A | 7/1995 | Schroeppel |
| 5,437,285 A | 8/1995 | Verrier et al. |
| 5,441,524 A | 8/1995 | Rueter et al. |
| 5,466,245 A | 11/1995 | Spinelli et al. |
| 5,469,859 A | 11/1995 | Tsoglin et al. |
| 5,480,412 A | 1/1996 | Mouchawar et al. |
| 5,490,323 A | 2/1996 | Thacker et al. |
| 5,501,702 A | 3/1996 | Plicchi et al. |
| 5,507,785 A | 4/1996 | Deno |
| 5,511,554 A | 4/1996 | Helfenbein et al. |
| 5,522,860 A | 6/1996 | Molin et al. |
| 5,524,632 A | 6/1996 | Stein et al. |
| 5,531,772 A | 7/1996 | Prutchi |
| 5,540,733 A | 7/1996 | Testerman et al. |
| 5,560,370 A | 10/1996 | Verrier et al. |
| 5,562,711 A | 10/1996 | Yerich et al. |
| 5,562,712 A | 10/1996 | Steinhaus et al. |
| 5,626,622 A | 5/1997 | Cooper |
| 5,626,624 A | 5/1997 | Schaldach et al. |
| 5,685,316 A | 11/1997 | Schookin et al. |
| 5,700,283 A | 12/1997 | Salo |
| 5,713,933 A | 2/1998 | Condie et al. |
| 5,718,235 A | 2/1998 | Golosarsky et al. |
| 5,718,720 A | 2/1998 | Prutchi et al. |
| 5,722,997 A | 3/1998 | Nedungadi et al. |
| 5,725,559 A | 3/1998 | Alt et al. |
| 5,749,900 A | 5/1998 | Schroeppel et al. |
| 5,755,671 A | 5/1998 | Albrecht et al. |
| 5,755,742 A | 5/1998 | Schuelke et al. |
| 5,766,225 A | 6/1998 | Kramm |
| 5,782,884 A | 7/1998 | Stotts et al. |
| 5,792,194 A | 8/1998 | Morra |
| 5,792,208 A | 8/1998 | Gray |
| 5,800,467 A | 9/1998 | Park et al. |
| 5,800,470 A | 9/1998 | Stein et al. |
| 5,817,135 A | 10/1998 | Cooper et al. |
| 5,817,136 A | 10/1998 | Nappholz et al. |
| 5,824,020 A | 10/1998 | Cooper |
| 5,824,029 A | 10/1998 | Weijand et al. |
| 5,836,975 A | 11/1998 | DeGroot |
| 5,836,976 A | 11/1998 | Min et al. |
| 5,836,987 A | 11/1998 | Baumann et al. |
| 5,842,997 A | 12/1998 | Verrier et al. |
| 5,873,897 A | 2/1999 | Armstrong et al. |
| 5,876,353 A | 3/1999 | Riff |
| 5,891,044 A | 4/1999 | Golosarsky et al. |
| 5,921,940 A | 7/1999 | Verrier et al. |
| 5,935,081 A | 8/1999 | Kadhiresan |
| 5,957,861 A | 9/1999 | Combs et al. |
| 5,974,340 A | 10/1999 | Kadhiresan |
| 5,978,707 A | 11/1999 | Krig et al. |
| 5,978,710 A | 11/1999 | Prutchi et al. |
| 5,987,356 A | 11/1999 | DeGroot |
| 6,006,134 A | 12/1999 | Hill et al. |
| 6,015,388 A | 1/2000 | Sackner et al. |
| 6,021,351 A | 2/2000 | Kadhiresan et al. |
| 6,022,322 A | 2/2000 | Prutchi |
| 6,026,320 A | 2/2000 | Carlson et al. |
| 6,035,233 A | 3/2000 | Schroeppel et al. |
| 6,042,548 A | 3/2000 | Giuffre |
| 6,044,294 A | 3/2000 | Mortazavi et al. |
| 6,049,735 A | 4/2000 | Hartley et al. |
| 6,058,331 A | 5/2000 | King |
| 6,073,048 A | 6/2000 | Kieval et al. |
| 6,076,015 A | 6/2000 | Hartley et al. |
| 6,135,970 A | 10/2000 | Kadhiresan et al. |
| 6,144,878 A | 11/2000 | Schroeppel et al. |
| 6,151,524 A | 11/2000 | Krig et al. |
| 6,161,042 A | 12/2000 | Hartley et al. |
| 6,179,865 B1 | 1/2001 | Hsu et al. |
| 6,193,668 B1 | 2/2001 | Chassaing et al. |
| 6,212,428 B1 | 4/2001 | Hsu et al. |
| 6,223,064 B1 | 4/2001 | Lynn et al. |
| 6,272,377 B1 | 8/2001 | Sweeney et al. |
| 6,273,856 B1 * | 8/2001 | Sun et al. ...................... 600/300 |
| 6,275,727 B1 | 8/2001 | Hopper et al. |
| 6,278,894 B1 | 8/2001 | Salo et al. |
| 6,317,632 B1 | 11/2001 | Krig et al. |
| 6,358,201 B1 | 3/2002 | Childre et al. |
| 6,370,424 B1 | 4/2002 | Prutchi |
| 6,371,922 B1 | 4/2002 | Baumann et al. |
| 6,390,986 B1 | 5/2002 | Curcie et al. |
| 6,411,840 B1 | 6/2002 | Bardy |
| 6,415,183 B1 | 7/2002 | Scheiner et al. |
| 6,430,435 B1 | 8/2002 | Hsu et al. |
| 6,445,951 B1 | 9/2002 | Mouchawar |
| 6,449,509 B1 | 9/2002 | Park |
| 6,456,871 B1 | 9/2002 | Hsu et al. |
| 6,459,929 B1 | 10/2002 | Hopper et al. |
| 6,463,326 B1 | 10/2002 | Hartley et al. |
| 6,473,640 B1 | 10/2002 | Erlebacher |
| 6,473,644 B1 | 10/2002 | Terry, Jr. et al. |
| 6,478,746 B2 | 11/2002 | Chassaing et al. |
| 6,480,733 B1 | 11/2002 | Turcott |
| 6,484,055 B1 | 11/2002 | Marcovecchio |
| 6,511,438 B2 | 1/2003 | Bernstein et al. |
| 6,511,500 B1 | 1/2003 | Rahme |
| 6,512,940 B1 | 1/2003 | Brabec et al. |
| 6,512,949 B1 | 1/2003 | Combs et al. |
| 6,520,924 B2 | 2/2003 | Lee |
| 6,522,914 B1 | 2/2003 | Huvelle et al. |
| 6,522,917 B1 | 2/2003 | Hsu et al. |
| 6,522,924 B1 | 2/2003 | Meier |
| 6,522,925 B1 | 2/2003 | Gilkerson et al. |

| | | |
|---|---|---|
| 6,522,926 B1 | 2/2003 | Kieval et al. |
| 6,526,313 B2 | 2/2003 | Sweeney et al. |
| 6,529,772 B2 | 3/2003 | Carlson et al. |
| 6,561,986 B2 | 5/2003 | Baura et al. |
| 6,571,121 B2 | 5/2003 | Schroeppel et al. |
| 6,571,122 B2 | 5/2003 | Schroeppel et al. |
| 6,574,506 B2 | 6/2003 | Kramer et al. |
| 6,575,916 B2 | 6/2003 | Halleck et al. |
| 6,589,188 B1 | 7/2003 | Street et al. |
| 6,611,713 B2 | 8/2003 | Schauerte |
| 6,647,289 B2 | 11/2003 | Prutchi |
| 6,687,540 B2 | 2/2004 | Marcovecchio |
| 6,690,971 B2 | 2/2004 | Schauerte et al. |
| 6,795,733 B1 | 9/2004 | Lu |
| 6,868,346 B2 | 3/2005 | Larson et al. |
| 6,928,324 B2 | 8/2005 | Park et al. |
| 6,931,281 B2 | 8/2005 | Bradley et al. |
| 7,010,349 B2 | 3/2006 | Conley et al. |
| 7,062,326 B2 | 6/2006 | Huvelle et al. |
| 7,092,757 B2 | 8/2006 | Larson et al. |
| 7,101,339 B2 | 9/2006 | Daum et al. |
| 7,136,705 B1 | 11/2006 | Park |
| 7,142,919 B2 | 11/2006 | Hine et al. |
| 7,200,440 B2 | 4/2007 | Kim et al. |
| 7,395,114 B2 | 7/2008 | Czygan et al. |
| 8,050,764 B2 | 11/2011 | Freeberg |
| 2002/0002389 A1 | 1/2002 | Bradley et al. |
| 2002/0026222 A1 | 2/2002 | Schauerte et al. |
| 2002/0049474 A1 | 4/2002 | Marcovecchio et al. |
| 2002/0058877 A1 | 5/2002 | Baumann et al. |
| 2002/0095189 A1 | 7/2002 | Andersson |
| 2002/0107552 A1 | 8/2002 | Krig et al. |
| 2002/0107553 A1 | 8/2002 | Hill et al. |
| 2002/0123768 A1 | 9/2002 | Gilkerson |
| 2002/0123769 A1 | 9/2002 | Panken et al. |
| 2002/0147475 A1 | 10/2002 | Scheiner et al. |
| 2002/0198461 A1 | 12/2002 | Hsu et al. |
| 2003/0032991 A1 | 2/2003 | Poore |
| 2003/0055461 A1 | 3/2003 | Girouard et al. |
| 2003/0060849 A1 | 3/2003 | Hsu |
| 2003/0069609 A1 | 4/2003 | Thompson |
| 2003/0105491 A1 | 6/2003 | Gilkerson et al. |
| 2003/0105499 A1 | 6/2003 | Hartley et al. |
| 2003/0109792 A1 | 6/2003 | Hsu et al. |
| 2003/0114889 A1 | 6/2003 | Huvelle et al. |
| 2003/0114891 A1 | 6/2003 | Hiebert et al. |
| 2003/0120316 A1 | 6/2003 | Spinelli et al. |
| 2003/0191503 A1 | 10/2003 | Zhu et al. |
| 2003/0216664 A1 | 11/2003 | Suarez |
| 2004/0015090 A1 | 1/2004 | Sweeney et al. |
| 2004/0039295 A1 | 2/2004 | Olbrich et al. |
| 2004/0049237 A1 | 3/2004 | Larson et al. |
| 2004/0093035 A1 | 5/2004 | Schwartz et al. |
| 2004/0102712 A1 | 5/2004 | Belalcazar et al. |
| 2004/0102908 A1 | 5/2004 | Larson et al. |
| 2004/0116820 A1 | 6/2004 | Daum et al. |
| 2004/0116742 A1 | 6/2004 | Marcovecchio |
| 2005/0004609 A1 | 1/2005 | Stahmann et al. |
| 2005/0004610 A1 | 1/2005 | Kim et al. |
| 2005/0065443 A1 | 3/2005 | Ternes |
| 2005/0080460 A1 | 4/2005 | Wang et al. |
| 2005/0096704 A1 | 5/2005 | Freeberg |
| 2005/0149135 A1 | 7/2005 | Krig et al. |
| 2005/0159781 A1 | 7/2005 | Hsu |
| 2005/0197674 A1 | 9/2005 | McCabe et al. |
| 2006/0020295 A1 | 1/2006 | Brockway et al. |
| 2006/0095083 A1 | 5/2006 | Zhang et al. |
| 2012/0046559 A1 | 2/2012 | Freeberg |

FOREIGN PATENT DOCUMENTS

| | | |
|---|---|---|
| EP | 0003567 | 8/1979 |
| EP | 0360412 | 3/1990 |
| EP | 0401962 | 12/1990 |
| EP | 447024 | 9/1991 |
| EP | 0555988 | 8/1993 |
| EP | 0597459 | 5/1994 |
| EP | 0617980 | 10/1994 |
| EP | 0709058 A1 | 1/1996 |
| EP | 702977 A | 3/1996 |
| EP | 744190 | 11/1996 |
| EP | 0748638 | 12/1996 |
| EP | 765632 | 4/1997 |
| EP | 0940155 | 9/1999 |
| FR | 2305168 | 10/1976 |
| WO | WO93/02746 | 2/1993 |
| WO | WO-9406512 | 3/1994 |
| WO | WO-98/14240 | 4/1998 |
| WO | WO-9943385 | 9/1999 |
| WO | WO-00/44274 | 8/2000 |
| WO | WO-0074775 A1 | 12/2000 |
| WO | WO-0078391 A1 | 12/2000 |
| WO | WO-03077759 A1 | 9/2003 |
| WO | WO-2006017446 A1 | 2/2006 |
| WO | WO-2006028575 A3 | 3/2006 |
| WO | WO-2006049767 A1 | 5/2006 |

OTHER PUBLICATIONS

"BioZ.com(tm) Noninvasive Hemodynamic Monitor", http://web/archive.org/web/20000617081457/http://www.cardiodynamics.com/cdprod10.html (archived Jun. 17, 2900), 2 pages.

"CardioDynamics BioZtect ICG Sensor & Cable System", http://web.archive.org/web/200107011105810/http://www.cardiodynamics.com/cdprod60.html, (archived Jul. 1, 2001),2 pages.

"CardioDynamics Company Overview", http://web.archive.org/web/20001121133300/http://www.cardiodynamics.com/cdcomp10.html, (archived Nov. 21, 2000),2 pages.

"Heart Rate Variability: Standards of Measurement, Physiological Interpretation, and Clinical Use", *European Heart Journal*, 17, Prepared by the Task Force of The European Society of Cardiology and The North American Society of Pacing and Electrophysiology; published by the American Heart Association, Inc.; European Society of Cardiology,(1996),pp. 354-381.

"Heart rate variability: standards of measurement, physiological interpretation and clinical use. Task Force of the European Society of Cardiology and the North American Society of Pacing and Electrophysiology", *Circulation*, 93(5), (Mar. 1, 1996), 1043-1065.

"Overview of Impedance Cardiography (ICG)", http://web.archive.org/web/20021003000713/http://www.impedancecariography.com/icgover10.html, (archived Oct. 3, 2002),5 Pages.

Alt, Eckhard, "What is the Ideal Rate-Adaptive Sensor for Patients with Implantable Cardioverter Defibrillators: Lessons from Cardiac Pacing", *American Journal of Cardiology*, 83(5B), (Mar. 11, 1999),17D-23D.

Barold, S., et al., "Contemporary issues in rate-adaptive pacing", *Clin. Cardiol.*, 20(8), (Aug. 1997),726-729.

Behrens, S., "Effects of Amiodarone on the Circadian Pattern of Sudden Cardiac Death (Department of Vererans Affairs Congestive Heart Failure-Survival Trial of Antiarrhythmic Therapy)", *Am. J. Cardiol.*, 80(1), (Jul. 1997),45-48.

Behrens, S., "Modification of the Circadian Pattern of Ventricular Tachyarrhythmias by Beta-Blocker Therapy", *Clin. Cardiol.*, 20(3), (Mar. 1997),253-257.

Berger, R. D., "An Efficient Algorithm for Spectral Analysis of Heart Rate Variability", *IEEE Transactions on Biomedical Engineering*, BME-33 (9), (Sep. 1986),900-904.

Bigger, J. T., "Correlations Among Time and Frequency Domain Measures of Heart Period Variability Two Weeks After Acute Myocardial Infarction", *Arrhythmias and Conduction Disturbances*, 69, (Apr. 1, 1992),891-898.

Bigger, Jr., J. T., "Spectral Analysis of R-R Variability to Evaluate Autonomic Physiology and Pharmacology and to Predict Cardiovascular Outcomes in Humans", *Diagnostic Evaluation*, Part XI, Chapter 101, 1151-1170.

Bilgutay, A M., "A new concept in the treatment of hypertension utilizing an implantable electronic device: "Baropacer"", *Trans Am Soc Artif Intern Organs.*, 10, (1964),387-395.

Bilgutay, A M., "Vagal tuning for the control of supraventricular arrhythmias", *Surgical Forum*, 16, (1965),151-3.

Bilgutay, Aydin M., "Vagal tuning. A new concept in the treatment of supraventricular arrhythmias, angina pectoris, and heart failure", *Journal of Thoracic and Cardiovascular Surgery*, 56(1), (Jul. 1968),71-82.

Bocker, D., "Ventricular Resynchronization Therapy May Restore Autonomic Balance as Evidenced by Redicung the Low Frequency to High Frequency Autonomic Ratio in Heart Failure Patients", *4th International Meeting organized by the Working Group on Heart Failure of the European Society of Cardiology (Abstract)*, Barcelona, Spain,(Jun. 11, 2001),1 p.

Borst, C , "Optimal frequency of carotid sinus nerve stimulation in treatment of angina pectoris", *Cardiovascular Research*, 8(5), (Sep. 1974),674-80.

Braunwald, E , "Carotid sinus nerve stimulation in the treatment of angina pectoris and supraventricular tachycardia", *California Medicine*, 112(3), (Mar. 1970),41-50.

Braunwald, E , "Relief of angina pectoris by electrical stimulation of the carotid-sinus nerves", *New England Journal of Medicine*, 277(24), (Dec. 14, 1967),1278-83.

Brockway, Marina , et al., "Method and Apparatus for Monitoring Heart Failure Patients With Cardiopulmonary Comorbidities", U.S. Appl. No. 10/897,856, filed Jul. 23, 2004, 54 pages.

Cha, Kichul , et al., "An electronic method for rapid measurement of haematocrit in blood samples", *Physiological Measurement*, 15 (2), (1994),129-137.

Cooper, Terry B., et al., "Neural effects on sinus rate and atrioventricular conduction produced by electrical stimulation from a transvenous electrode catheter in the canine right pulmonary artery", *Circulation Research*, vol. 46, No. 1, (Jan. 1980),48-57.

Courtice, G P., "Effect of frequency and impulse pattern on the non-cholinergic cardiac response to vagal stimulation in the toad, Bufo marinus", *Journal of the Autonomic Nervous System*, 48(3), (Aug. 1994),267-72.

Crawford, Michael H., "ACC/AHA Guidelines for Ambulatory Electrocardiography", *JACC*, vol. 34, No. 3, Published by Elsevier Science Inc.,(Sep. 1999),912-948.

Dart Jr., C H., "Carotid sinus nerve stimulation treatment of angina refractory to other surgical procedures", *Annals of Thoracic Surgery*, 11(4), (Apr. 1971), 348-59.

De Landsheere, D , "Effect of spinal cord stimulation on regional myocardial perfusion assessed by positron emission tomography", *American Journal of Cardiology*69(14), (May 1, 1992), 1143-9.

Epstein, S E., "Treatment of angina pectoris by electrical stimulation of the carotid-sinus nerves", *New England Journal of Medicine*, 280(18), (May 1, 1969), 971-8.

Euler, D. E., et al., "Inspiration induced by phrenic nerve stimulation increases defribillation energy requirements", *PACE*(22), Part II, Abstract No. 307, (1999), 777.

Farrehi, C , "Stimulation of the carotid sinus nerve in treatment of angina pectoris", *American Heart Journal*, 80(6), (Dec. 1970),759-65.

Feliciano, L , "Vagal nerve stimulation releases vasoactive intestinal peptide which significantly increases coronary artery blood flow", *Cardiovascular Research*, 40(1), (Oct. 1998),45-55.

Freeberg, S. , "Automatically Configurable Minute Ventilation Sensor", U.S. Appl. No. 10/735,598, filed Dec. 12, 2003, 35 pgs.

Freeberg, S. , "Cross-Checking of Transthoracic Impedance and Acceleration Signals", U.S. Appl. No. 10/696,729, filed Oct. 29, 2003, 27 pgs.

Fromer, M , "Ultrarapid subthreshold stimulation for termination of atrioventricular node reentrant tachycardia", *Journal of the American College of Cardiology*, 20(4), (Oct. 1992),879-83.

Gilkerson, James O., et al., "System and Method for Detection Enhancement Programming", U.S. Appl. No. 11/369,142, filed Mar. 6, 2006, 43 pgs.

Hauck, John O., "A Minute Ventilation Sensor Derived from Intrathoracic Electric Impedance as a Cardiac Pacemaker Rate Modulator", *University of Minnesota Master Thesis*, (Jun. 1993), pp. 80-86 & 97.

Hayano, J. , "Circadian Rhythms of Atrioventricular Conduction Properties in Chronic Atrial Fibrillation With and Without Heart Failure", *JACC*, 31 (1), (Jan. 1998), pp. 158-166.

Hayano, J. , et al., "Respiratory sinus arrhythmia: a phenomenon improving pulmonary gas exchange and circulatory efficiency", *Circulation*, 94(4), (1996),842-847.

Henning, R J., "Effects of autonomic nerve stimulation, asynchrony, and load on dP/dtmax and on dP/dtmin", *American Journal of Physiology*, 260(4 Pt 2), (Apr. 1991),H1290-8.

Henning, R J., "Vagal nerve stimulation increases right ventricular contraction and relaxation and heart rate", *Cardiovascular Research*, 32(5), (Nov. 1996),846-53.

Henning, R J., "Vagal stimulation attenuates sympathetic enhancement of left ventricular function", *American Journal of Physiology*, 258(5 Pt 2), (May 1990),H1470-5.

Hsu, William , "System and Method for Classifying Tachycardia Arrhythmias Having 1:1 Atrial to Ventricular Rhythms", U.S. Appl. No. 09/417,588, filed on Oct. 13, 1999, 39 pgs.

Jackson, Leland B., "Chapter 11 / Quantization Effects", *Digital Filters and Signal Processing*, 2d Edition, Kluwer Academic Publishers,(1989), pp. 297-340.

Jessurun, G A., "Coronary blood flow dynamics during transcutaneous electrical nerve stimulation for stable angina pectoris associated with severe narrowing of one major coronary artery", *American Journal of Cardiology*, 82(8), erratum appears in Am J Cardiol Feb. 15, 1999;83(4):642,(Oct. 15, 1998), 921-926.

Johnston, P. W., et al., "The transthoracic impedance cardiogram is a potential haemodynamic sensor for an automated external defibrillator", *European Heart Journal*, 19(12), (Dec. 1998),1879-1888.

Kadhiresan, Veerichetty , et al., "Cardiopulmonary functional status assessment via heart rate response detection by implantable cardiac device" U.S. Appl. No. 10/914,632, filed Aug. 9, 2004, 18 pgs.

Kim, J. , et al., "Cardiac Cycle Synchronized Sampling of Impedance Signal", U.S. Appl. No. 10/612,388, filed Jul. 2, 2003, 28 pgs.

Krig, David B., "Apparatus and Method for Treating Ventricular Tachyarrhythmias", U.S. Appl. No. 11/073,818, filed Mar. 7, 2005, 61 pgs.

Larson, Dennis E., et al., "Minute Ventilation Sensor With Automatic High Pass Filter Adjustment", U.S. Appl. No. 10/306,889, filed Nov. 27, 2002, 33 pages.

Lavery, C. E., "Nonuniform Nighttime Distribution of Acute Cardiac Events", *Circulation*, 96(10), (Nov. 18, 1997),3321-3327.

Lincoln, William C., "Classifying Tachyarrhythmia Using Time Interval Between Ventricular Depolarization and Mitral Valve Closure", U.S. Appl. No. 10/618,261, filed Jul. 11, 2003, 26 pgs.

Maasrani, M. , et al., "Continuous Measurements by Impedance of Haematocrit and Plasma Volume Variations During Dialysis", *Medical & Biological Engineering & Computing*35 (3), (May 1997),167-171.

Mannheimer, C , "Epidural spinal electrical stimulation in severe angina pectoris", *British Heart Journal*, 59(1), (Jan. 1988),56-61.

Mannheimer, C , "Transcutaneous electrical nerve stimulation (TENS) in angina pectoris", *Pain*, 26(3), (Sep. 1986),291-300.

Mannheimer, C , "Transcutaneous electrical nerve stimulation in severe angina pectoris", *European Heart Journal*, 3(4), (Aug. 1982),297-302.

Mazgalev, T N., "Autonomic modification of the atrioventricular node during atrial fibrillation: role in the slowing of ventricular rate", *Circulation*, 99(21), (Jun. 1, 1999),2806-14.

McCabe, Aaron , "Self-Diagnostic Method and System for Implantable Cardiac Device", U.S. Appl. No. 10/890,810, filed Jul. 14, 2004, 18 pgs.

Murphy, D F., "Intractable angina pectoris: management with dorsal column stimulation", *Medical Journal of Australia*, 146(5), (Mar. 2, 1987),260.

Peckova, M. , "Circadian Variations in the Occurence of Cardiac Arrests", *Circulation*, 98 (1), (1998),pp. 31-39.

Peters, T K., "Temporal and spatial summation caused by aortic nerve stimulation in rabbits. Effects of stimulation frequencies and amplitudes", *Journal of the Autonomic Nervous System*, 27(3), (Aug. 1989),193-205.

Peters, T K., "The principle of electrical carotid sinus nerve stimulation: a nerve pacemaker system for angina pectoris and hypertension therapy", *Annals of Biomedical Engineering*, 8(4-6), (1980),445-58.

Ponikowski, P. , et al., "Oscillatory Implications and Role of Augmented Peripheral Chemosensitivity", *Circulation*, 100, (1999),2418-2424.

Pop, G. A., et al., "Catheter-based Impedance Measurements in the Right Atrium for continuuously monitoring Hematocrit and Estimating blood Viscosity Changes; an in vivo Feasibility Study in Swine", *Biosensors and Bioelectronics*, 19 (12), (Jul. 15. 2004),1685-1693.

Rickards, Anthony, et al., "An implantable intracardiac accelerometer for monitoring myocardial contractility. The Multicenter PEA Study Group", *Pacing Clin Electrophysiol.*, 19(12) (Pt 1), (Dec. 1996),2066-2071.

Ruiter, J H., et al., "Adaptive rate pacing controlled by the right ventricular preejection interval: clinical experience with a physiological pacing system", *Pacing Clin Electrophysiol.*, 15(6), (Jun. 1992),886-94.

Salo, Rodney W., "Continuous ventricular volume assessment for diagnosis and pacemaker control", *Pacing Clin Electrophysiol.*, 7(6 Pt 2), (Nov. 1984),1267-1272.

Salo, Rodney W., "Measurement of ventricular volume by intracardiac impedance: theoretical and empirical approaches", *IEEE Transactions on Biomedical Engineering*, 33(2), (Feb. 1986),189-195.

Salo, R W., "The theoretical basis of a computational model for the determination of volume by impedance", *Automedica*, 11, (1989),299-310.

Schaldach, M., "Automatic adjustment of pacing parameters based on intracardiac impedance measurements", Pacing Clin Electrophysiol., 13(12 Pt 2), (Dec. 1990), 1702-1710.

Schaldach, M, et al., "Intracardiac impedance to determine sympathetic activity in rate responsive pacing", *Pacing Clin Electrophysiol.*, 15(11 Pt 2), (Nov. 1992),1778-86.

Schauerte, P, "Catheter stimulation of cardiac parasympathetic nerves in humans: a novel approach to the cardiac autonomic nervous system", *Circulation*, 104(20), (Nov. 13, 2001),2430-5.

Schauerte, Patrick N., et al., "Transvenous parasympathetic cardiac nerve stimulation: an approach for stable sinus rate control", *Journal of Cardiovascular Electrophysiology*, 10(11). (Nov. 1999),1517-24.

Schauerte, Patrick N., "Transvenous Parasympathetic Nerve Stimulation in the Inferior Vena Cava and Atrioventricular Conduction", *Journal of Cardiovascular Electrophysiology*, 11(1), (Jan. 2000),64-69.

Schauerte, P, "Ventricular rate control during atrial fibrillation by cardiac parasympathetic nerve stimulation: a transvenous approach", *Journal of the American College of Cardiology*, 34(7), (Dec. 1999),2043-50.

Scherlag, M A., "Endovascular Neural Stimulation Via a Novel Basket Electrode Catheter: Comparison of Electrode Configurations", *Journal of Interventional Cardiac Electrophysiology*, 4(1), (Apr. 2000),219-224.

Smith, V., "Systems, Devices and Methods for Tachyarrythmia Discrimination or Therapy Decisions", U.S. Appl. No. 10/897,365, filed Jul. 22, 2004, 38 pgs.

Stahmann, J. E., et al., "Implantable Devices and Methods Using Frequency-Domain Analysis of Thoracic Signal", U.S. Appl. No. 10/612,387, filed Jul. 2, 2003, 39 pgs.

Sweeney, R. J., et al., "Device for Monitoring Fluid Status", U.S. Appl. No. 10/909,926, filed Aug. 2, 2004, 17 pgs.

Takahashi, N, "Vagal modulation of ventricular tachyarrhythmias induced by left ansae subclaviae stimulation in rabbits", *Japanese Heart Journal*, 39(4), (Jul. 1998),503-11.

Vanoli, Emilio, "Vagal stimulation and prevention of sudden death in conscious dogs with a healed myocardial infarction", *Circulation Research*, vol. 68, No. 4, (May 1991).1471-1481.

Wallick, D W., "Selective AV nodal vagal stimulation improves hemodynamics during acute atrial fibrillation in dogs", *American Journal of Physiology—Heart & Circulatory Physiology*281(4), (Oct. 2001),H1490-7.

Waninger, M S., "Electrophysiological control of ventricular rate during atrial fibrillation", *Pacing & Clinical Electrophysiology*, 23(8), (Aug. 2000),1239-44.

Yamashita, T., "Circadian Variation of Paroxysmal Atrial Fibrillation", Circulation, 96 (5), (Sep. 2, 1997),pp. 1537-1541.

Zhang, Yi, et al., "Methods and Apparatuses for Arrhythmia Detection and Classification Using Wireless ECG", U.S. Appl. No. 10/975,166, filed Oct. 28, 2004, 69 pgs.

Zhang, Y, "Optimal ventricular rate slowing during atrial fibrillation by feedback AV nodal-selective vagal stimulation", *American Journal of Physiology—Heart & Circulatory Physiology*282(3), (Mar. 2002).H1102-10.

Zhou, X, "Prevention of high incidence of neurally mediated ventricular arrhythmias by afferent nerve stimulation in dogs", *Circulation*, 101(7), (Feb. 22, 2000),819-24.

"U.S. Appl. No. 10/319,794, Non Final Office Action mailed Nov. 8, 2005", 9 pgs.

"U.S. Appl. No. 10/319,794, Notice of Allowance mailed Apr. 21, 2006", 7 pgs.

"U.S. Appl. No. 10/319,794, Response filed Jan. 24, 2006 to Non Final Office Action mailed Nov. 8, 2005", 13 pgs.

"U.S. Appl. No. 10/319,794, Supplemental Notice of Allowability mailed Jun. 15, 2006", 2 pgs.

"U.S. Appl. No. 10/359,820, Non Final Office Action mailed Jun. 10, 2004", 6 pgs.

"U.S. Appl. No. 10/359,820, Notice of Allowance mailed Mar. 10, 2005", 7 pgs.

"U.S. Appl. No. 10/359,820, Notice of Allowance mailed Oct. 4, 2004", 7 pgs.

"U.S. Appl. No. 10/359,820, Notice of Allowance mailed Nov. 23, 2005", 7 pgs.

"U.S. Appl. No. 10/359,820, Response filed Sep. 10, 2004 to Non Final Office Action mailed Jun. 10, 2004", 8 pgs.

"U.S. Appl. No. 10/696,729, Response filed Jul. 11, 2011 to Final Office Action mailed May 5, 2010", 9 pgs.

"U.S. Appl. No. 10/696,729, Final Office Action mailed May 10, 2011", 7 pgs.

"U.S. Appl. No. 10/696,729, Non Final Office Action mailed Nov. 26, 2010", 7 pgs.

"U.S. Appl. No. 10/696,729, Response filed Feb. 28, 2011 to Non Final Office Action mailed Nov. 26, 2010", 14 pgs.

"U.S. Appl. No. 10/696,729, Response filed Apr. 6, 2009 to Restriction Requirement mailed Mar. 4, 2009", 11 pgs.

"U.S. Appl. No. 10/696,729, Notice of Allowance mailed Aug. 9, 2011", 7 pgs.

"U.S. Appl. No. 13/285,560, Non-Final Office Action mailed Mar. 7, 2012", 8 pgs.

* cited by examiner

CARDIAC CYCLE SYNCHRONIZED SAMPLING OF IMPEDANCE SIGNAL

RELATED APPLICATIONS

This application is a Continuation of Ser. No. 10/612,388, now U.S. Pat. No. 7,200,440, filed on Jul. 2, 2003, which is incorporated herein by reference.

TECHNICAL FIELD

This document relates generally to implantable devices, and, in particular, to a system and method for obtaining transthoracic impedance information.

BACKGROUND

Many systems implantable into a patient's thorax include a pulse generator and an arrangement of endocardial or intravascular leads (hereinafter referred to as "leads"). The pulse generator delivers electrical stimuli to tissue via the leads to provide a desired therapy. For example, implantable pacemakers deliver timed sequences of low energy electrical stimuli, called pace pulses, to the heart via an intravascular lead. By properly timing the delivery of pace pulses, the heart can be induced to contract in proper rhythm, greatly improving its pumping efficiency. Implantable defibrillators are devices capable of delivering higher energy electrical stimuli to the heart. A defibrillator is capable of delivering a high-energy electrical stimulus via leads that is sometimes referred to as a defibrillation countershock. The countershock interrupts a fibrillation, allowing the heart to reestablish a normal rhythm for efficient pumping of blood. These systems are able to sense cardiac signals and deliver therapy to the heart based on such signals.

The arrangement of the leads of such systems in the thorax region allows for other physiologic signals to be sensed. One type of physiologic signal is the transthoracic (i.e. across the chest) impedance of a patient with such a device. One approach to measure transthoracic impedance is described in Hartley et al., U.S. Pat. No. 6,076,015 "RATE ADAPTIVE CARDIAC RHYTHM MANAGEMENT DEVICE USING TRANSTHORACIC IMPEDANCE," assigned to the assignee of the present application and which is incorporated herein by reference. The transthoracic impedance signal includes multiple components. A first component of the impedance varies with a patient's breathing and is useful in determining how fast (breathing rate) or how deeply (lung tidal volume) a patient is breathing. Information concerning a patient's breathing over a period of time is useful to an implantable pacemaker system as a metabolic indication that the patent's heart rate needs to be adjusted. However, the measurement of this respiratory component of the transthoracic impedance is complicated by other components of the impedance signal. For example, transthoracic impedance also varies with the volume of blood in a patient's heart and thus varies during a patient's heartbeat or cardiac cycle. This component is sometimes referred to as the cardiac stroke volume. This stroke volume component is close in frequency to the respiratory component. The closeness of the frequencies makes it difficult to separate the two components from each other. Previous solutions to the problem have used filtering circuitry to remove all but the breathing component of the transthoracic signal. However, because implantable systems are battery powered and are implanted for long periods of time, methods that perform a function with lower power consumption extending the battery life are valuable in such systems. Thus there is a need for a device and method to measure the respiratory component of the transthoracic impedance that has low power consumption.

SUMMARY

This document discusses a cardiac rhythm management device and method for obtaining impedance information from a thorax region of a patient. The device comprises a sensor for obtaining a signal indicative of an action of a heart, an impedance measurement circuit adapted to measure transthoracic impedance and a processor for utilizing the signal indicative of the action of the heart to sample the transthoracic impedance at sampling intervals commenced by fiducial markers in the signal indicative of the action of the heart, where the sampling of the impedance signal removes the component of a stroke volume of the heart from the signal and thereby providing lung ventilation information.

The method of measuring a transthoracic impedance comprises detecting intrinsic heart activity signals, applying a predetermined pulsed current stimulus across a thorax region of a patient in a predetermined time relationship to a fiducial marker, sampling a voltage across the thorax region when applying the predetermined pulsed current stimulus, and calculating an impedance from the measured voltage and the predetermined pulsed current stimulus.

This summary is intended to provide an overview of the subject matter of the present application. It is not intended to provide an exclusive or exhaustive explanation of the invention. The detailed description is included to provide further information about the subject matter of the preset patent application.

BRIEF DESCRIPTIONS OF THE DRAWINGS

In the drawings like numerals refer to like components throughout the several views.

DETAILED DESCRIPTION

In the following detailed description, reference is made to the accompanying drawings which form a part hereof, and in which is shown by way of illustration specific embodiments in which the invention may be practiced. It is to be understood that other embodiments may be utilized and structural changes may be made without departing from the scope of the present invention.

As discussed previously, the measurement of the respiratory component of the transthoracic impedance is complicated by the presence of the stroke volume component of the impedance signal. Because the stroke volume component is present due to the filling and emptying of the heart with blood, this component is synchronized to heartbeats. Implantable systems are able to sense intrinsic activity signals associated with heartbeats. The implantable systems are further able to generate fiducial markers in response to occurrences of such an activity signals. As an example, one of these activity signals is a QRS complex. A QRS complex is the activity signal associated with the process of the ventricular chambers depolarizing or contracting to empty the chambers of blood. In general, the volume of blood in the heart at an occurrence of an activity signal is fairly consistent from one occurrence of the signal to the next. Thus, the stroke volume component of the transthoracic impedance will also be fairly consistent at each occurrence of the signal. If the transthoracic impedance is sampled synchronously only when the implantable system generates a specific fiducial marker, the stroke volume component will be constant during the sampling and the respiratory signal is easily extracted from the transthoracic impedance signal. Examples of intrinsic heart activity signals sensed by implantable systems and useful for sampling include an onset of a P-wave, an onset of a QRS complex, an R-wave peak, or a T-wave peak.

Figure 1:
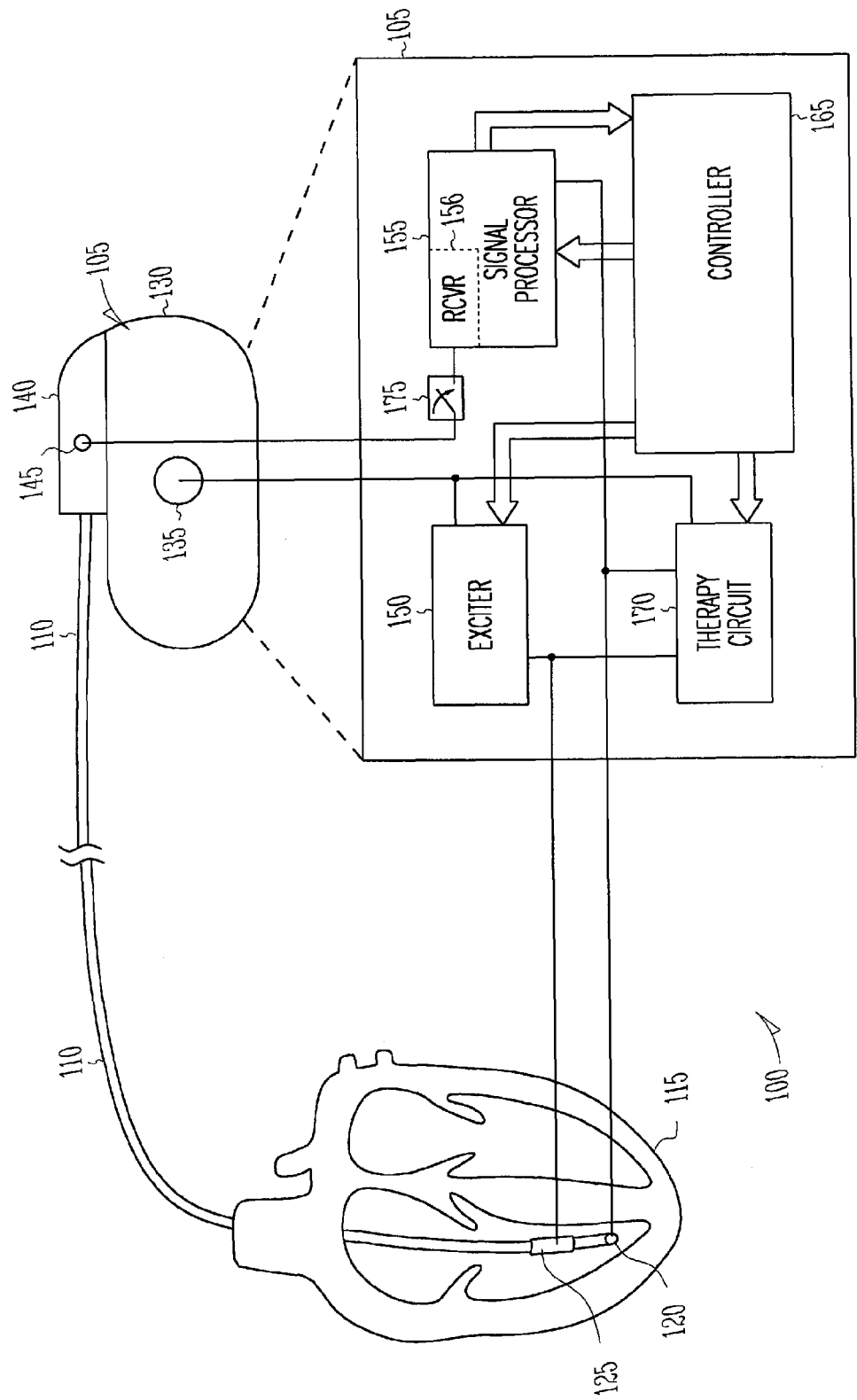
FIG. 1 shows a block diagram of a cardiac rhythm management system that samples transthoracic impedance in a predetermined time relationship to a fiducial marker.

FIG. 1 shows one embodiment of a system 100 for sampling the transthoracic impedance commenced at the occurrence of a fiducial marker. This embodiment of the system includes pulse generator 105 and endocardial lead 110. Lead 110 is shown coupled to pulse generator 105. Lead 110 is a multi-conductor lead and includes tip electrode 120 coupled to a first conductor and ring electrode 125 coupled to a second lead conductor. Pulse generator 105 includes a hermetically sealed outer housing 130. Outer housing 130 (sometimes referred to as the case or can) is comprised of a conducting material such as titanium, and is covered by an insulating material such as silicone rubber. A hole or window in the insulating material allows a third electrode 135 to be formed from the can 130 of pulse generator 105.

Pulse generator 105 also includes a header 140 for receiving the lead 110 and is formed from an insulating material such as molded plastic. Header 140 also includes a fourth electrode 145. Such a four-electrode system is described in Hauck et al., U.S. Pat. No. 5,284,136 "DUAL INDIFFERENT ELECTRODE PACEMAKER," assigned to the assignee of the present application and which is incorporated herein by reference. Other embodiments of the system include a two or three electrode system. In the embodiment shown, lead 110 is implanted in the right ventricle of a heart 115. In this embodiment, the impedance sampling may begin, for example, at a fiducial marker indicating the onset of a QRS complex, at a fiducial marker indicating a peak of the R-wave, or at a fiducial marker indicating a peak of the T-wave.

FIG. 1 also illustrates portions of pulse generator 105. Therapy circuit 170 provides electrical pacing stimuli to the heart 115. Such pacing stimuli include providing bipolar pacing between tip electrode 120 and ring electrode 125 to initiate a contraction of the ventricles. Controller 165 adjusts the rate of the pacing stimuli delivered by the therapy circuit 170. Signal Processor 155 senses an intrinsic heart activity signal. When signal processor 155 senses the onset of an intrinsic heart activity signal, controller 165 initiates an impedance measurement. Exciter 150 delivers an electrical excitation signal, such as a pulsed current stimulus or any other suitable measurement stimulus, to heart 115. In one embodiment, exciter 150 delivers a predetermined current stimulus between ring electrode 125 and can electrode 135. In other embodiments exciter 150 delivers a current stimulus between any other suitable combinations of electrodes. Signal processor 155 senses the response to the excitation signal. In one embodiment, signal processor 155 senses the response between tip electrode 120 and header electrode 145. In other embodiments, signal processor 155 senses the response between any other suitable combinations of electrodes. Receiver 156 of the signal processor 155 receives a voltage through sampling element 175 in response to the onset of an intrinsic heart activity signal and the current stimulus. In the embodiment shown sampling element 175 is placed in series with header electrode 145 and the receiver 156. In another embodiment the sampling element is placed in series with the lead electrodes 120, 125 and the receiver 156. The signal processor 155 then measures the voltage by any method known in the art such as by an Analog to Digital converter. Transthoracic impedance is obtained from the predetermined current stimulus and the measured voltage. The transthoracic impedance may then be used to determine respiratory information.

Figure 2:
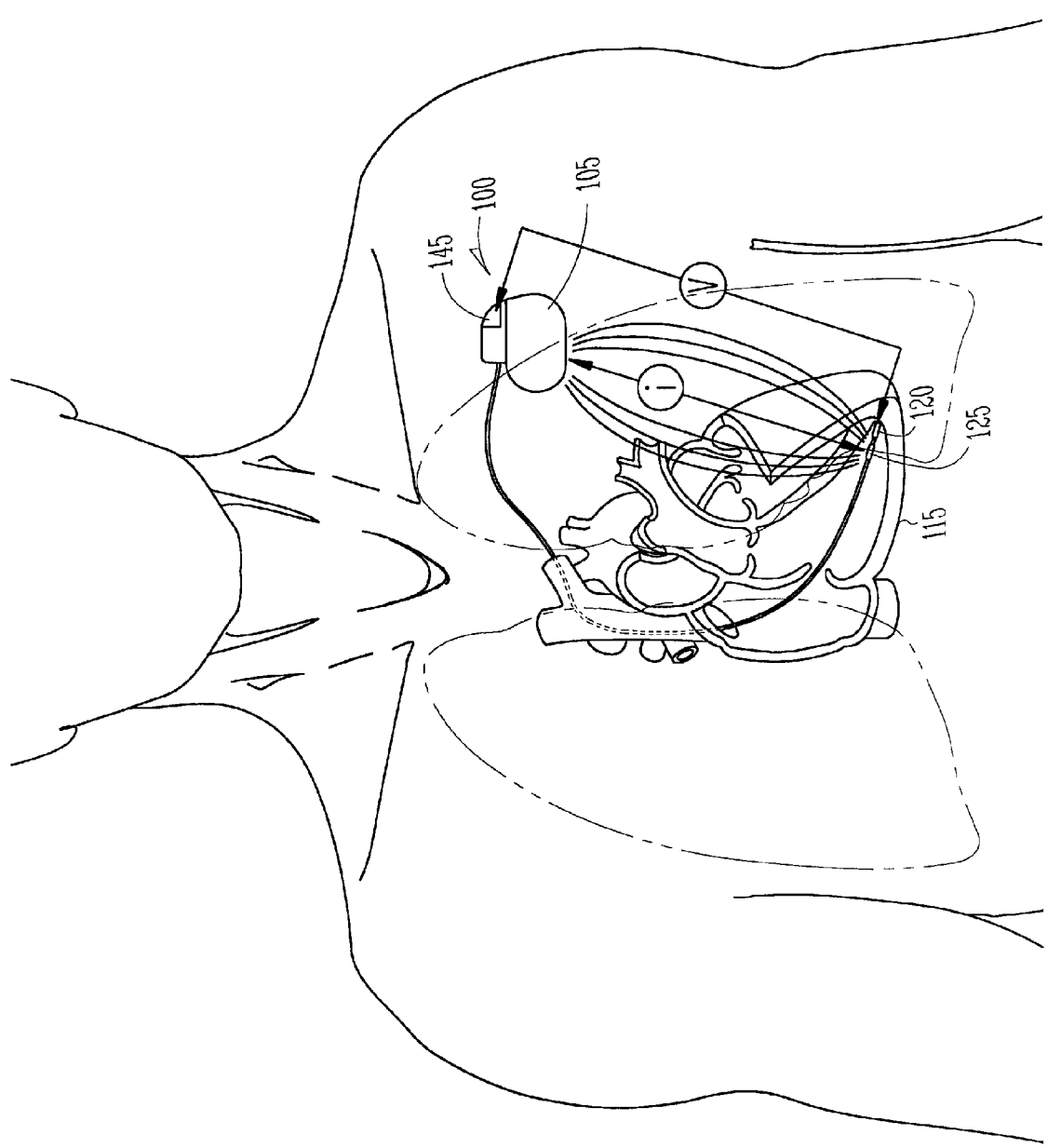
FIG. 2 illustrates an embodiment of the system implanted in a thorax region.

FIG. 2 illustrates the system 100 implanted in the thorax region of a patient. It can be seen from the positioning of pulse generator 105 and lead electrodes 120 and 125 that the system 100 measures the impedance across a substantial portion of the patient's thorax. In one embodiment of the system 100, a time index is stored along with the impedance value obtained. The time index and impedance value are then used to derive a lung tidal volume. As discussed in the Hartley patent, lung tidal volume is obtained by taking the difference between the maximum and minimum impedance values stored for the patient's previous breath. A larger tidal volume value indicates a deeper breath for the patient than a smaller tidal volume value. In another embodiment, respiratory rate is derived from the impedance signal. One method to obtain respiratory rate would be to determine the time interval between maximum impedance values over a period of time and convert the data to breaths per minute. Based on information from the lung tidal volume and respiratory rate, controller 165 adjusts the rate of the delivery of therapy to the heart 115. A further embodiment of the system 100 is a combination of cardiac rhythm management and treatment for sleep apnea. In this embodiment, the system 100 determines if the respiratory activity falls below a predetermined level. If the respiratory activity falls below the predetermined level, the system provides therapy to treat the sleep apnea such as diaphragmatic pacing. An apparatus for diaphragmatic pacing to treat sleep apnea is described in Scheiner et al., U.S. Pat. No. 6,415,183 "A METHOD AND APPARATUS FOR DIAPHRAGMATIC PACING," assigned to the assignee of the present application and which is incorporated herein by reference.

Figure 3:
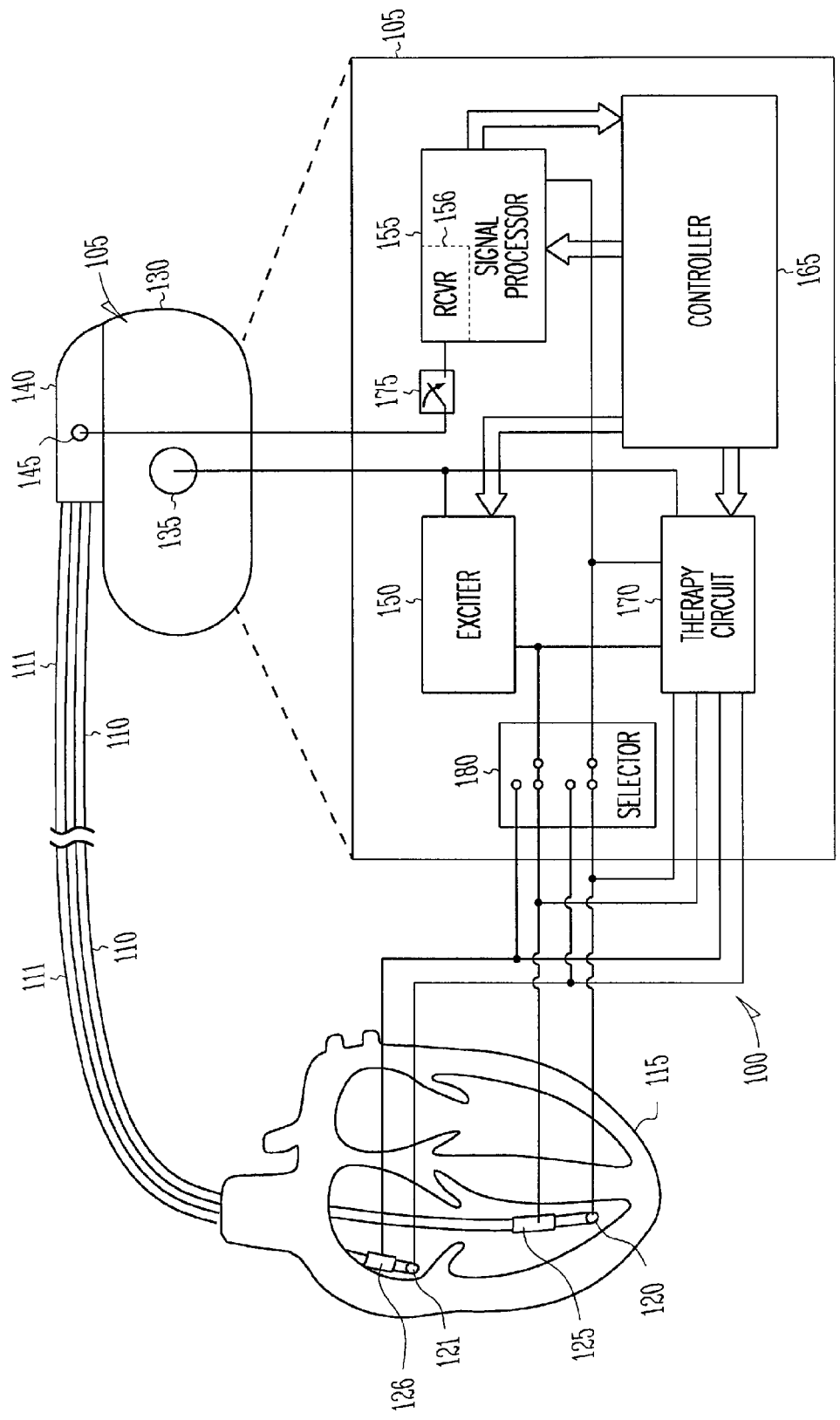
FIG. 3 shows a block diagram of a multi-lead embodiment of the system.

FIG. 3 shows an embodiment of the system 100 that uses multiple endocardial leads 100, 111. Leads 110, 111 are multi-conductor leads and include tip electrodes 120, 121 coupled to a first conductor and ring electrodes 125, 126 coupled to a second lead conductor within their respective lead. In the embodiment shown, lead 110 is implanted in the right ventricle of a heart 115 and lead 111 is implanted in the right atrium of the heart. If lead 111 is used to measure the impedance, the impedance sampling may begin, for example, at a fiducial marker indicating the onset of the P-wave rather than the QRS complex or the peak of an R-wave.

This embodiment of the system 100 further shows a pulse generator 105 that includes selector 180. Selector 180 is able to change the electrode combination providing the stimulus from a combination including ring electrode 125 to a combination including ring electrode 126. Selector 180 also changes the electrode combination measuring the stimulus response from a combination including tip electrode 120 to a combination including tip electrode 121. This ability to change the electrode combination is useful if, for example, measuring the sensed response using tip electrode 120 proves to be difficult due to signal noise, and use of another combination of electrodes provides a better measurement. It should be noted that other embodiments of the system 100 deliver the current stimulus or measure the response between any other suitable combinations of electrodes.

Figure 4:
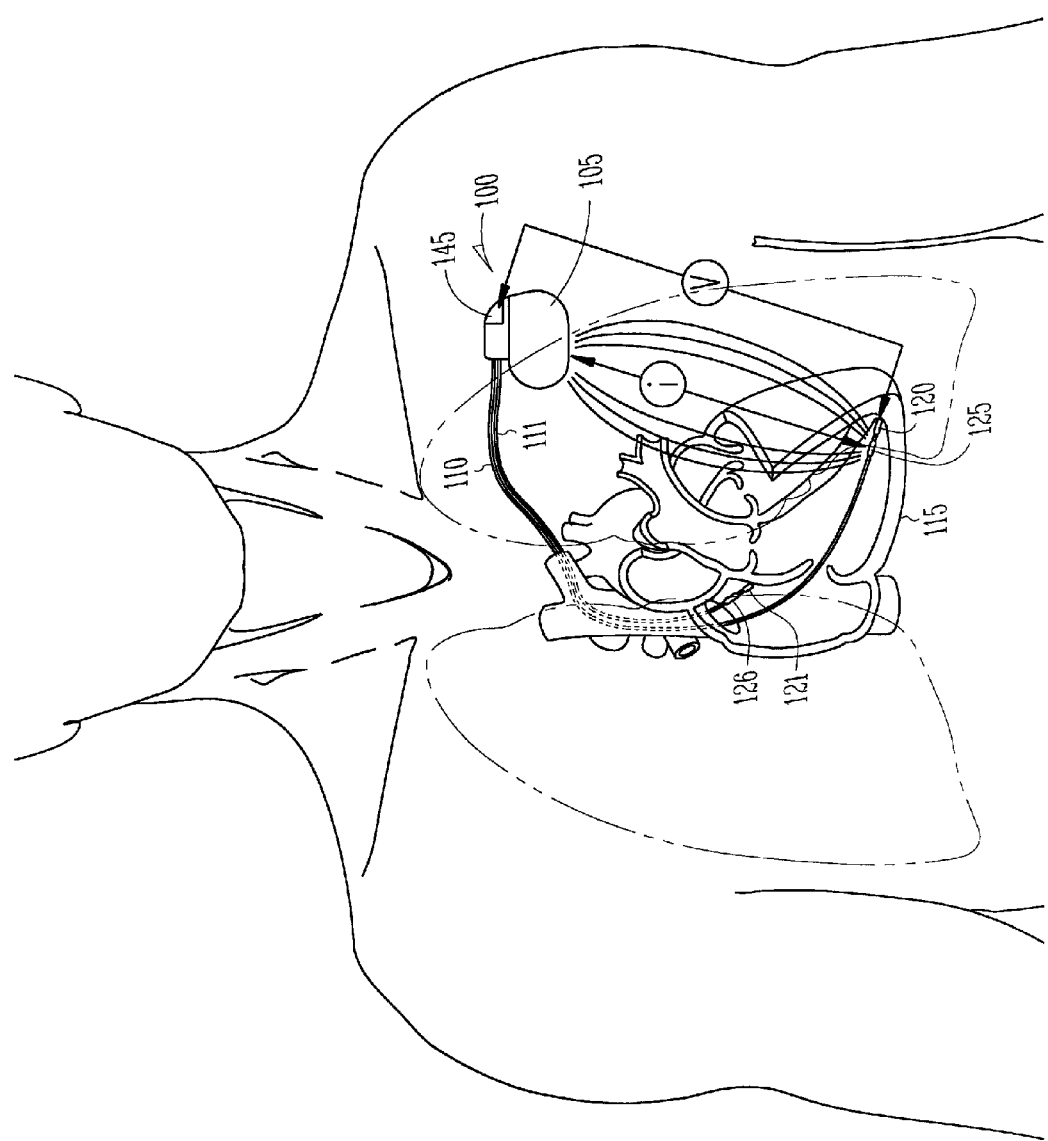
FIG. 4 illustrates a multi-lead embodiment of the system implanted in a thorax region.

FIG. 4 illustrates a multiple lead embodiment of the system 100 implanted in the thorax region of a patient. It can be seen from the positioning of pulse generator 105 and lead electrodes 120, 121 and 125, 126 that the system 100 measures the impedance across a substantial portion of the patient's thorax. It can also be seen that selecting different combinations of electrodes will result in an impedance measurement taken across different vectors of the thorax. For example, using tip and ring electrodes 121, 126 and header and can electrodes 145, 135 will measure impedance across a vector originating from the atrium, while using tip and ring electrodes 120, 125 and can electrodes 145, 135 will measure impedance across a vector originating from the ventricle. Thus, it is beneficial for the system 100 to have flexibility in its measurement configuration to take full advantage of its positioning.

Figure 5:
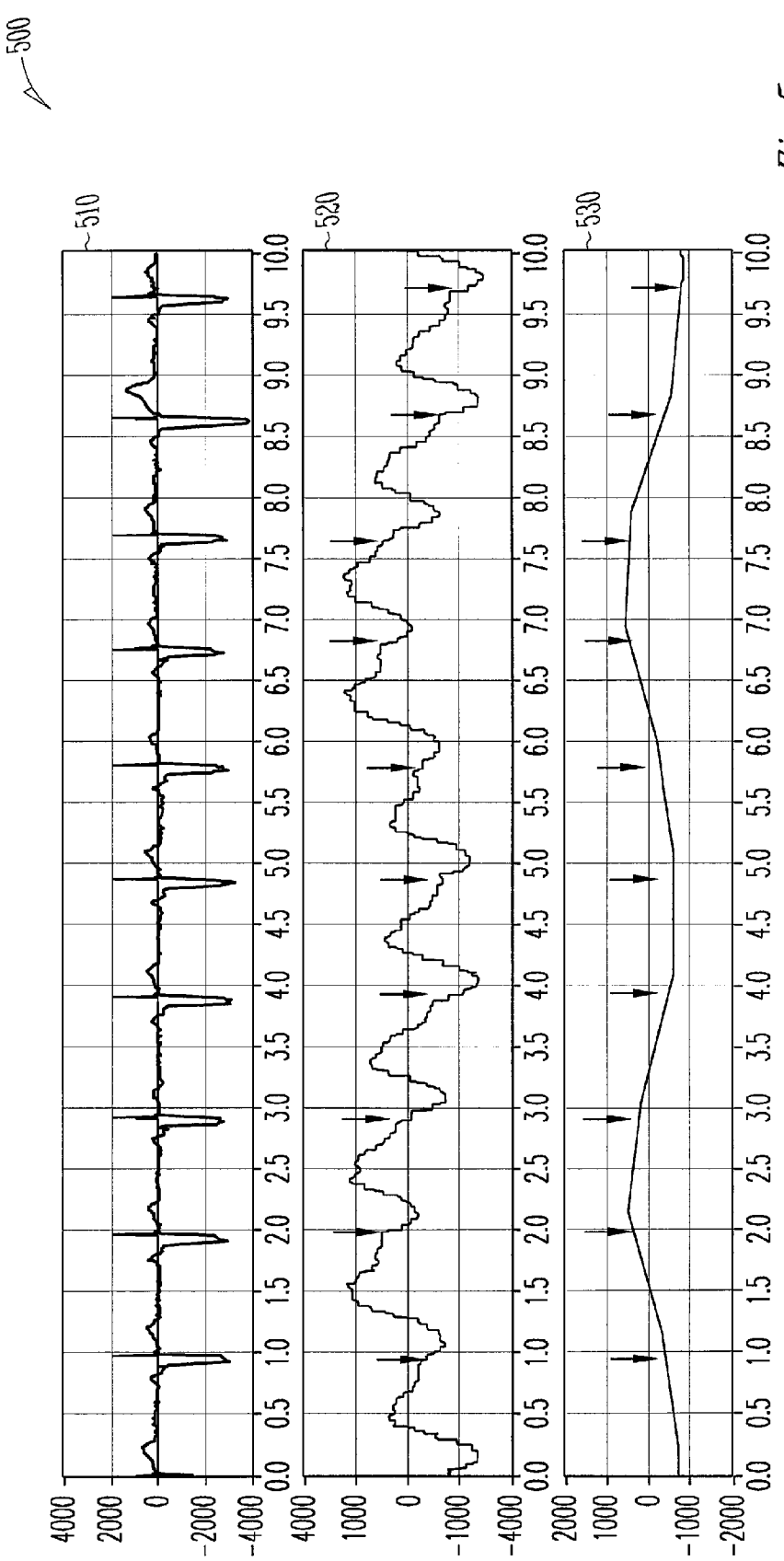
FIG. 5 is a representation of a transthoracic impedance signal sampled in a predetermined time relationship to a fiducial marker.

FIG. 5 is a graphical illustration 500 of sampling the transthoracic impedance synchronously to fiducial markers that indicate R-wave peaks. QRS complexes from heart activity are shown in graph 510. In graph 520, a transthoracic impedance signal obtained by sampling every 50 milliseconds is shown. The variation of the impedance signal with cardiac stroke volume can be seen. It can also be seen that the higher frequency stroke volume component is superimposed onto a lower frequency respiratory component. The downwardly pointing arrows shown in graph 520 correspond to the occurrence of R-waves in graph 510. Graph 530 shows the impedance signal obtained when the impedance is sampled synchronously to the R-waves. Graph 530 shows that the lower frequency respiratory signal is extracted from the higher frequency stroke volume component.

Figure 6:
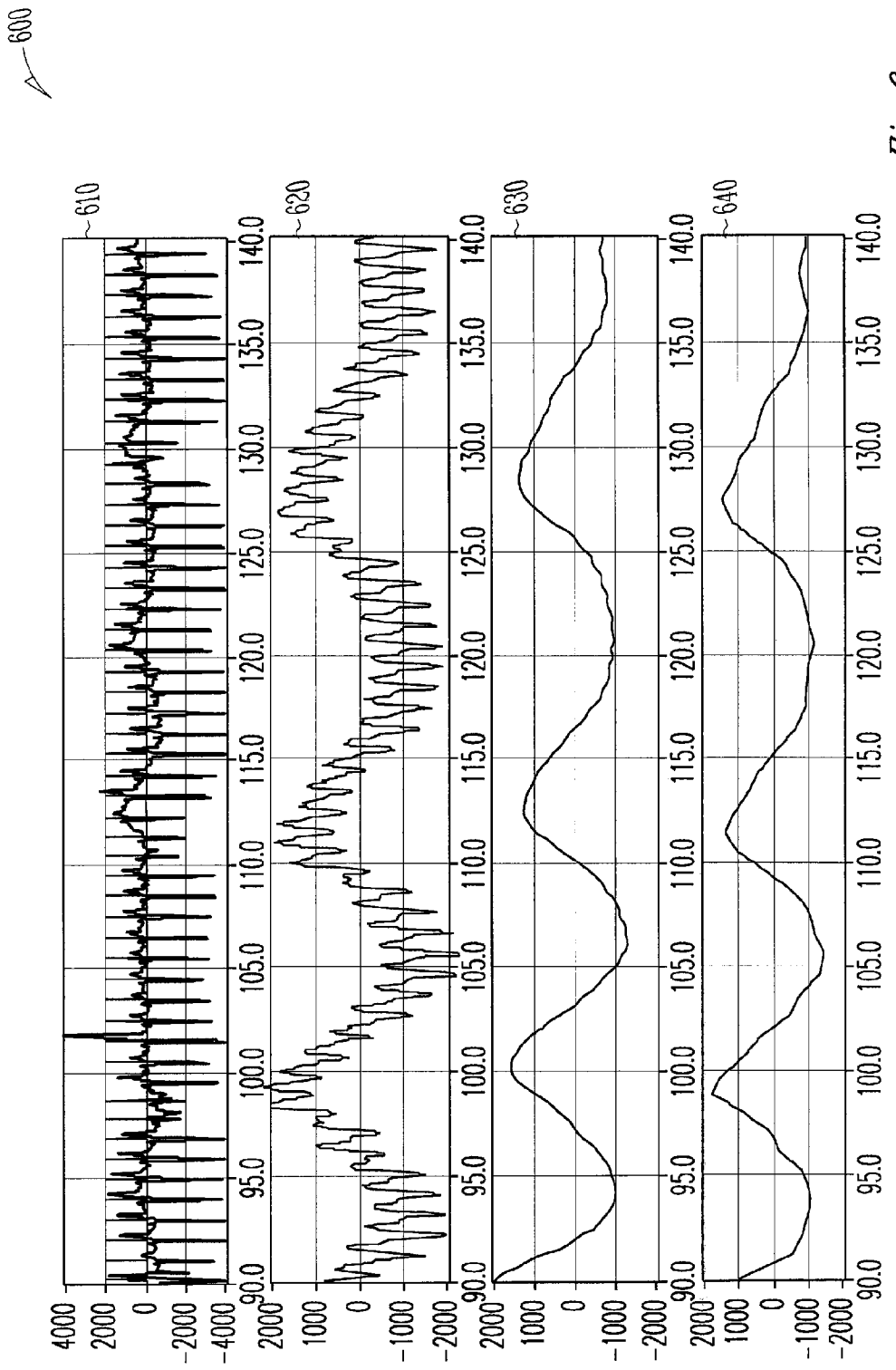
FIG. 6 is an illustration of a filtered transthoracic impedance signal compared to an R-wave synchronized sampled impedance signal during deep and slow breathing.

FIG. 6 is a graphical illustration 600 of sampling the transthoracic impedance during deep and slow breathing. Graph 610 shows the R-waves from heart activity. Graph 620 shows the transthoracic impedance signal obtained by sampling at a frequency high enough to obtain both the stroke volume and the respiratory component. Graph 630 shows the respiratory component obtained through sampling and filtering with a $4^{th}$-order Elliptic Low Pass Filter with the filter pole at 0.2 Hertz(Hz). In implantable devices, such filters are generally implemented with active circuits. While these circuits can be designed to operate at low power, even low power circuits have an appreciable effect on battery life when the implanted period is on the order of five years. Graph 640 shows the respiratory component obtained with R-wave synchronous sampling. Graphs 630 and 640 show that similar results are obtained concerning phase, amplitude and frequency using the low pass filtering method and the R-wave sampling method. Thus, similar results for impedance measurements at slow and deep breathing can be attained while conserving the power required by an active low pass filtering circuit.

Figure 7:
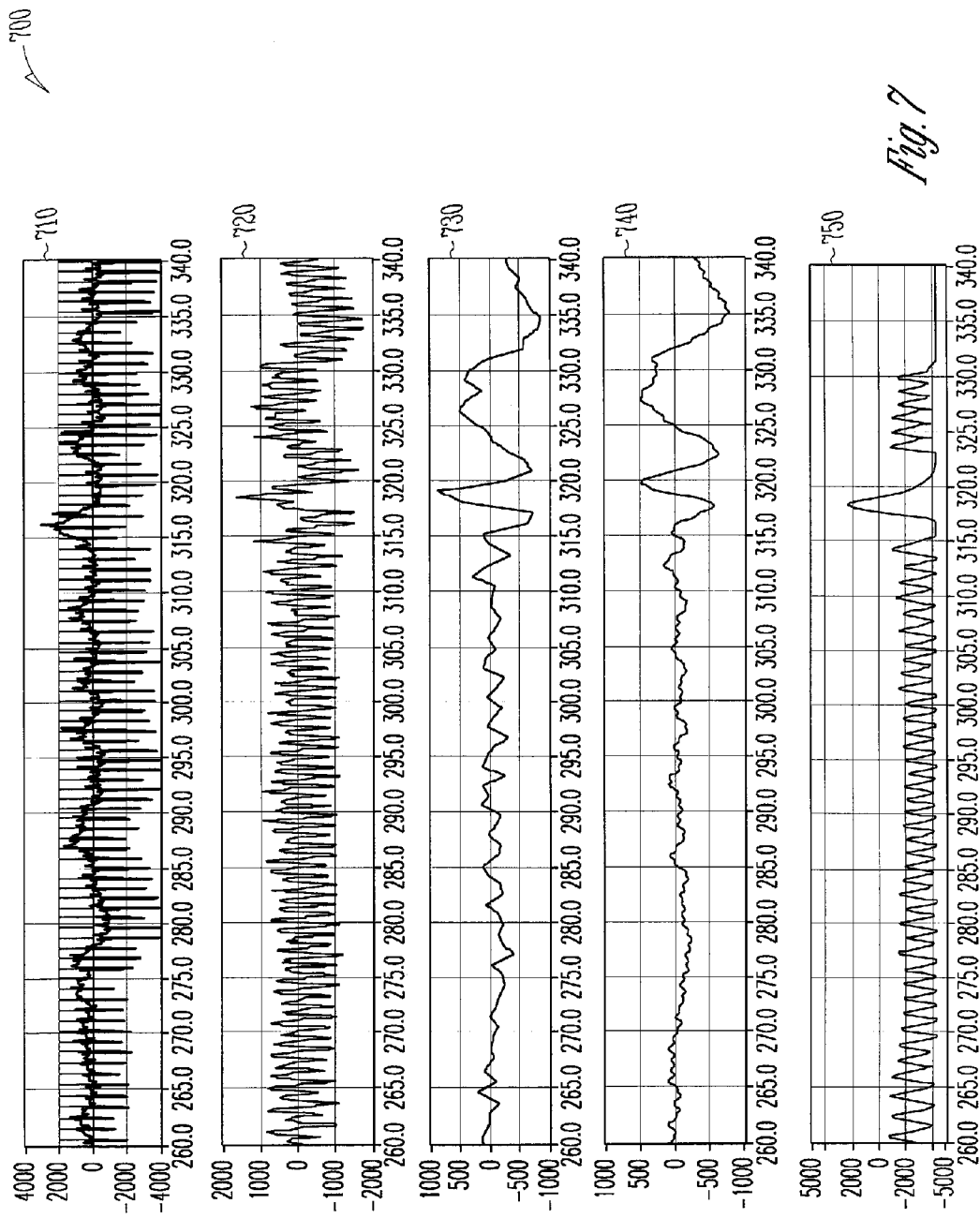
FIG. 7 is an illustration of a filtered transthoracic impedance signal compared to an R-wave synchronized sampled impedance signal during fast and shallow breathing.

FIG. 7 is a graphical illustration 700 of sampling the transthoracic impedance during fast and shallow breathing. Graph 710 shows the R-waves of heart activity. Graph 720 shows the transthoracic impedance signal obtained by sampling at a frequency high enough to obtain both the stroke volume and the respiratory component. Graph 730 shows the respiratory component obtained with R-wave synchronous sampling. Graph 740 shows the respiratory component obtained from the high frequency sampling filtering with a $4^{th}$-order Elliptic Low Pass Filter with the filter pole at 0.2 Hertz (Hz). Graph 750 shows the actual measured air volume passing through the lungs of the patient. A comparison of graphs 740 and 750 shows that in attempting to capture the transthoracic impedance during fast and shallow breathing, a 0.2 Hz pole can mask some of the impedance information as the frequency of the respiratory activity approaches the frequency of the stroke volume. Graph 730 shows that R-wave synchronous sampling has some advantage in reproducing amplitude information. This is because the sampling increases with the heart rate of the patient. Thus, somewhat improved results for impedance measurements at fast and shallow breathing can be attained while conserving the power required by an active low pass filtering circuit.

Figure 8:
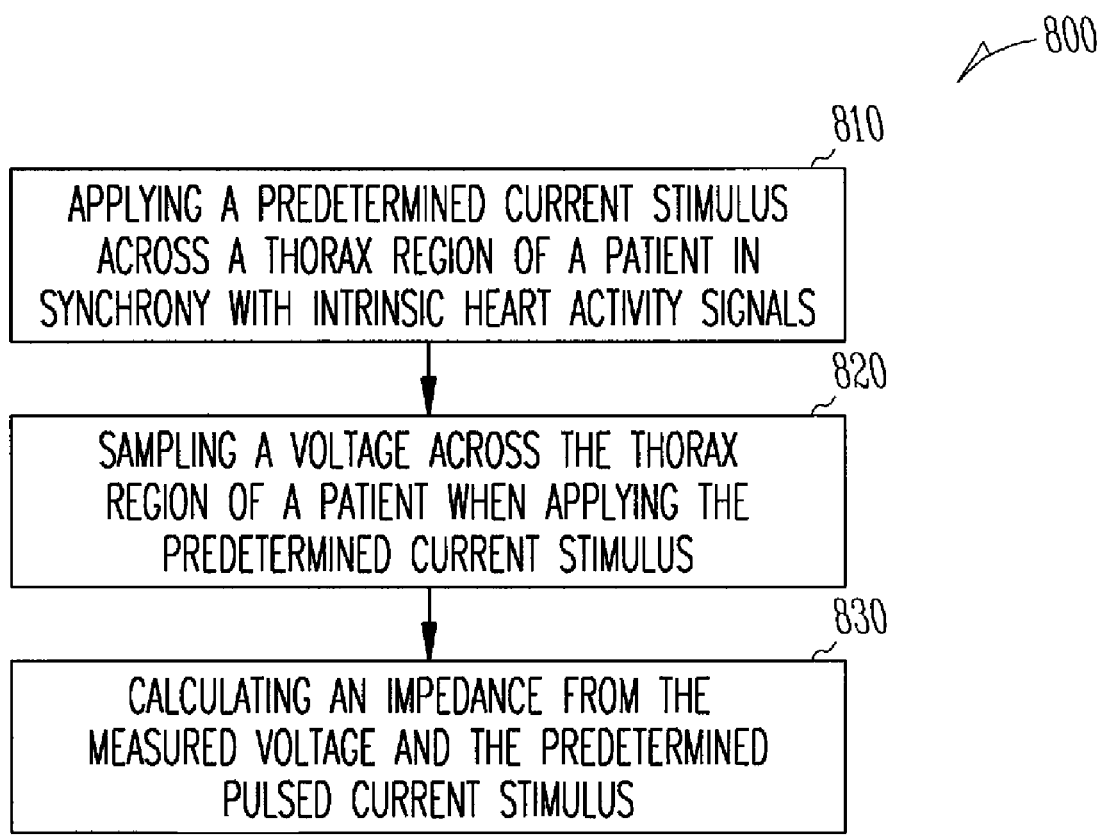
FIG. 8 is a flow chart illustrating a method of measuring transthoracic impedance.

FIG. 8 is a flow chart illustrating a method 800 of measuring transthoracic impedance. At 810, a predetermined pulsed current stimulus is applied across a thorax region of a patient in synchrony with intrinsic heart activity signals. At 820, a voltage across the thorax region is sampled when applying the predetermined pulsed current stimulus. At 830, impedance is calculated from the measured voltage and the predetermined pulsed current stimulus.

Figure 9:
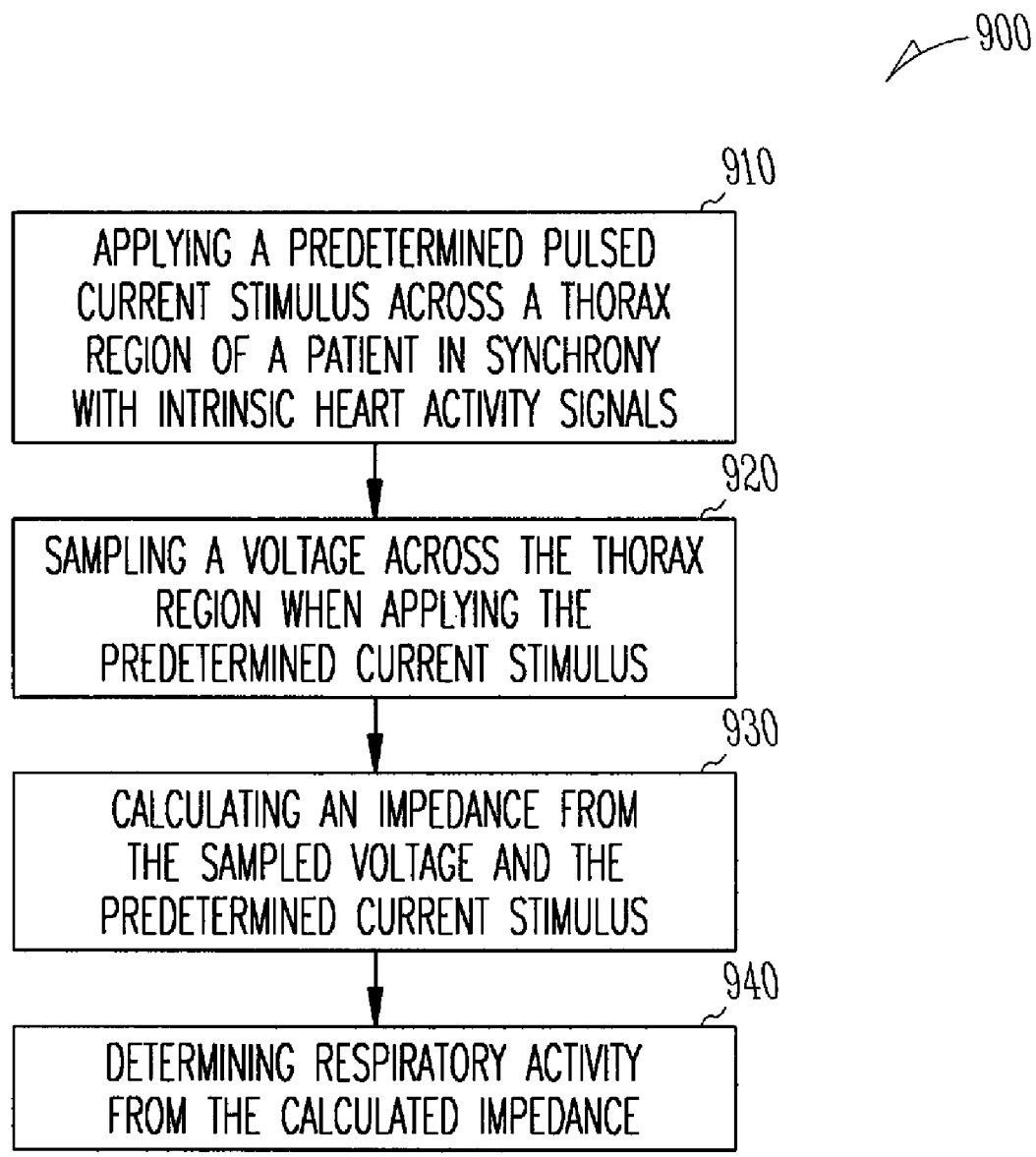
FIG. 9 is a flow chart illustrating a method of monitoring lung ventilation.

FIG. 9 is a flow chart illustrating a method of monitoring lung ventilation. At 910, a predetermined pulsed current stimulus is applied across a thorax region of a patient in synchrony with intrinsic heart activity signals. At 920, a voltage across the thorax region is sampled when applying the predetermined current stimulus. At 930, impedance is calculated from the sampled voltage and the predetermined current stimulus. At 940, respiratory activity is determined from the calculated impedance.

Although specific examples have been illustrated and described herein, it will be appreciated by those of ordinary skill in the art that any arrangement calculated to achieve the same purpose could be substituted for the specific example shown. This application is intended to cover any adaptations or variations of the present invention. Therefore, it is intended that this invention be limited only by the claims and the equivalents shown.

What is claimed is:

1. A cardiac management system comprising:
   an implantable device, including:
      a memory circuit;
      an intrinsic cardiac signal sensor;
      an impedance measurement circuit configured for generating a sampled transthoracic impedance signal; and
      a processor, coupled to the intrinsic cardiac signal sensor and the impedance measurement circuit, the processor configured to:
         initiate sampling of a transthoracic impedance signal substantially at an instance of a fiducial marker in a sensed intrinsic cardiac signal, the sampling to attenuate or remove a cardiac stroke component from the transthoracic impedance signal and to preserve a respiratory component of the transthoracic impedance signal; and
         measure a time interval between successive occurrences of the fiducial marker indicative of a cardiac cycle and to store a value in the memory circuit representative of the sampled measured transthoracic impedance in correspondence with an indication of the measured time interval; and determine lung information using the sampled measured transthoracic impedance in correspondence with an indication of the measured time interval.

2. The system claim 1, wherein the fiducial marker includes an R-wave peak.

3. The system of claim 1, wherein the processor is configured to determine ventilation information using the respiratory component of the transthoracic impedance signal.

4. The system of claim 3, wherein the processor is configured to combine sampled values of transthoracic impedance signal to reconstruct a signal indicative of respiratory activity.

5. The system of claim 1, including a memory communicatively coupled to the processor, and wherein the processor is configured to measure a time interval from a past occurrence of the fiducial marker to a present occurrence of the fiducial marker and to store a value in the memory representative of the measured impedance in association with the measured time interval.

6. The system of claim 1, wherein the implantable device is configured for estimating lung tidal volume using the sampled measured transthoracic impedance in correspondence with an indication of the measured time interval.

7. The system of claim 5, wherein the implantable device is configured for determining a respiratory rate using the stored value representative of the measured impedance.

8. The system of claim 1, wherein the impedance measurement circuit includes:
an exciter configured for delivering a pulsed current stimulus to at least two electrodes;
a sampling circuit, coupled to the processor, configured to provide the sampled transthoracic impedance signal in response to instances of the fiducial marker; and
at least one endocardial lead coupled to the implantable device and configured for placement in a plurality of locations in a thorax of a patient for delivering electrical energy thereto, wherein the endocardial lead includes at least a first implantable electrode.

9. The system of claim 8, including a housing for the implantable device, an outer surface of the housing further comprising a second implantable electrode.

10. The system of claim 8, including a header, coupled to the housing to receive the endocardial lead, and carrying a header electrode comprising a second implantable electrode.

11. The system of claim 8, wherein the implantable device includes a plurality of endocardial leads and a selector, wherein the selector is configured for coupling the exciter and processor to a selected endocardial lead, wherein the exciter is coupled to the first electrode of the endocardial lead and the processor is coupled to a different electrode, such that selecting a different lead causes the exciter to apply the pulsed current stimulus as a different vector in a thorax.

12. The system of claim 8, wherein the implantable device includes:
an electrical stimuli delivery circuit, coupled to at least one electrode; and
a controller, coupled to the therapy circuit for adjusting a rate of delivery of the electrical stimuli using the respiratory component of the transthoracic impedance signal.

13. The system claim 1, wherein the fiducial marker includes an onset of a P-wave.

14. The system claim 1, wherein the fiducial marker includes an onset of a QRS complex.

15. The system claim 1, wherein the fiducial marker includes a T-wave peak.

16. A method of measuring transthoracic impedance with an implantable medical device, the method comprising:
sensing an intrinsic cardiac signal;
generating a transthoracic impedance signal;
sampling the transthoracic impedance signal substantially at an instance of a fiducial marker in the sensed intrinsic cardiac signal, wherein the sampling removes a cardiac stroke component from the transthoracic impedance signal and preserves a respiratory component of the transthoracic impedance signal;
measuring a time interval between successive occurrences of the fiducial marker indicative of a cardiac cycle;
storing a value representative of the sampled measured transthoracic impedance in correspondence with an indication of the measured time interval; and
determining lung information using the sampled measured transthoracic impedance in correspondence with an indication of the measured time interval.

17. The method of claim 16, wherein the fiducial marker includes an R-wave peak.

18. The method of claim 16, wherein the fiducial marker includes an onset of a P-wave.

19. The method of claim 16, wherein the fiducial marker includes an onset of a QRS complex.

20. The method of claim 16, wherein the fiducial marker includes a T-wave peak.

21. The method of claim 16, wherein sampling the transthoracic impedance signal includes:
detecting fiducial markers in the sensed intrinsic cardiac signal;
applying a pulsed current stimulus in a specified time relationship to an occurrence of a fiducial marker;
sampling a voltage resulting from the pulsed current stimulus, such that a component of the voltage from a cardiac stroke volume is substantially constant; and
calculating an impedance from the sampled voltage and the pulsed current stimulus.

22. The method of claim 21, wherein the sampling a voltage includes changing the sampling rate according to a change in heart rate.

23. The method of claim 21 including:
providing respiratory activity information from the calculated impedance; and
providing a therapy for stimulating breathing activity if the respiratory activity information indicates the respiratory activity falls below a specified level.

24. The method of claim 16, wherein the method includes:
storing data representing the transthoracic impedance;
measuring a time interval from a first occurrence of the fiducial marker to a second occurrence of the fiducial marker; and
storing the time interval in association with the data representing the transthoracic impedance.

25. The method of claim 24, comprising estimating a lung tidal volume using the sampled measured transthoracic impedance in correspondence with an indication of the measured time interval.

26. The method of claim 16, including:
providing ventilation information using the respiratory component of the transthoracic impedance signal; and
using the ventilation information for changing a therapy delivered in a system for treating cardiac arrhythmia.

* * * * *